United States Patent [19]
Ohlson

[11] Patent Number: 5,157,707
[45] Date of Patent: Oct. 20, 1992

[54] METHOD AND A CASSETTE HOLDER FOR PERFORMING X-RAY EXAMINATION

[75] Inventor: Carl-Eric Ohlson, Stockholm, Sweden

[73] Assignee: AO Medical Products AB, Stockholm, Sweden

[21] Appl. No.: 752,623

[22] PCT Filed: Feb. 15, 1990

[86] PCT No.: PCT/SE90/00104
§ 371 Date: Aug. 20, 1991
§ 102(e) Date: Aug. 20, 1991

[87] PCT Pub. No.: WO90/09147
PCT Pub. Date: Aug. 23, 1990

[30] Foreign Application Priority Data
Feb. 20, 1989 [SE] Sweden ................ 8900581

[51] Int. Cl.$^5$ ............................................. G03B 42/04
[52] U.S. Cl. ..................................... 378/181; 378/182; 378/167; G03B/42/04
[58] Field of Search ............... 378/178, 169, 170, 167, 378/168, 175, 181, 182, 187, 198, 180, 195

[56] References Cited
U.S. PATENT DOCUMENTS

| | | | |
|---|---|---|---|
| 2,264,410 | 12/1941 | Schier | 378/195 |
| 2,651,725 | 9/1953 | McFarland | 250/58 |
| 2,939,008 | 5/1960 | Goodfriend | 378/181 |
| 3,154,683 | 10/1964 | Blair | 250/50 |
| 3,778,625 | 12/1973 | Schwartz et al. | 378/180 |
| 3,795,815 | 3/1974 | Weinstock et al. | 250/444 |
| 4,468,803 | 8/1984 | Ronci | 378/181 |

Primary Examiner—Constantine Hannaher
Assistant Examiner—Don Wong
Attorney, Agent, or Firm—Fleit, Jacobson, Cohn, Price, Holman & Stern

[57] ABSTRACT

In connection with X-ray or like examination there is used a cassette holder arrangement which is carried by a frame structure (7) by means of pivotal arms (4) which are capable of being swung in the horizontal plane, such as to adjust the position of the cassette in the vertical direction. The arrangement enables pictures to be taken of a sitting patient in mutually perpendicular directions, with the aid of a radiation source (2). The cassette holder (3) can be swung between the exposure positions in a circuit path around the sitting patient, by activation of one of the arms (4). To this end there can be used a parallel linkage (11) which is operative to guide the cassette holder during this pivotal movement. the cassette holder is fixated relative to one of the arms (4), by means of a locking device (8), which is released when wishing to pivot the cassette holder. The invention also relates to a cassette holder arrangement of the aforedescribed kind.

8 Claims, 2 Drawing Sheets

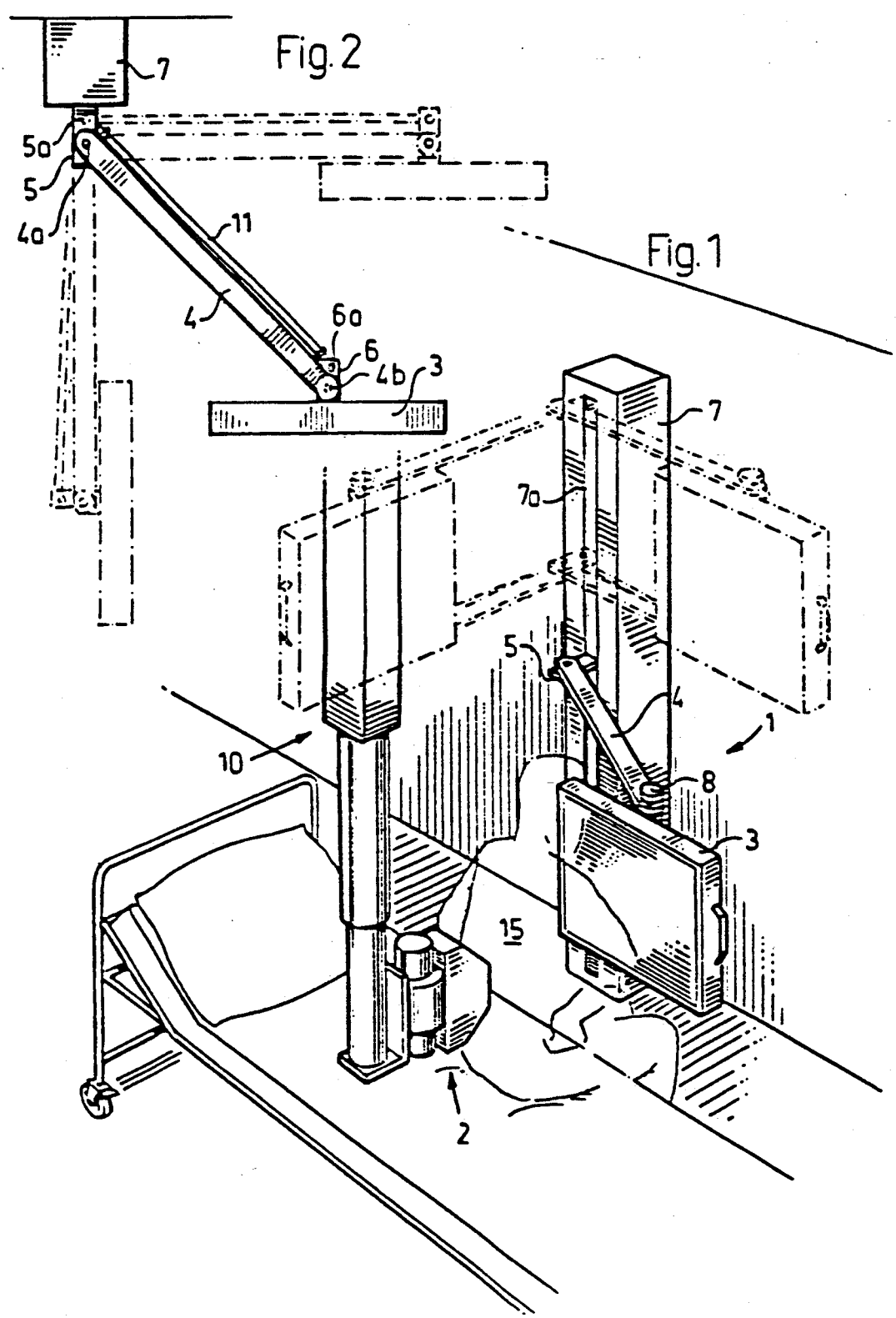

METHOD AND A CASSETTE HOLDER FOR PERFORMING X-RAY EXAMINATION

FIELD OF INVENTION

The present invention relates to a method for carrying out X-ray examinations or like examinations with the aid of a cassette-carried receptor intended to receive radiation from a radiation source which is adapted to take two or more exposures.

The invention also relates to a cassette-holder device for carrying out such diagnostics.

Particular problems are encountered, both on the part of the patient and on the part of the personnel, when subjecting to X-ray examination elderly patients, who are often seriously handicapped, and other categories of patients who have difficulty in leaving their hospital bed on their own feet, e.g. because of serious illness or injury sustained in a traffic accident for instance. In some cases it is necessary to X-ray a patient at the beside with the patient in bed, requiring the image receptor to be placed between the patient and the mattress, with all the drawbacks associated therewith.

Bedside examinations are carried out both in intensive care wards, using portable X-ray equipment, and in the X-ray department itself.

The majority of patients who are either too ill or too weak to stand unsupported or unaided are, nevertheless, able to sit on the edge of the bed. Although some lung X-ray frames will permit frontal pictures to be taken from the bed, no room is available for side pictures, since the lung frame is normally placed adjacent a wall which makes it impossible to turn the bed through an angle of 90°.

BACKGROUND ART

Various methods and cassette holders have been proposed with the intention of facilitating the X-ray examination of handicapped patients.

For instance, U.S. Pat. No. 4,468,803 (Ronci) describes a cassette-holder suspension system which enables the cassette holder to be rotated in mutually different planes so as to enable different types of exposures to be taken. This known system include a clamping device which is maneuvered with the aid of knobs and by means of which the cassette holder and carrier means can be brought to different desired positions, for instance adjacent a table. Vertical adjustments can be made only by releasing the clamping device and mounting said device at the height desired. One drawback with this known apparatus is that it is heavy to manipulate, particularly when moving the apparatus between different positions of application.

U.S. Pat. No. 2,651,725 (McFarland) describes a similar cassette holder device which can be mounted in different positions adjacent a patient's bed. Adjustments require the manipulation or activation of a relatively large number of clamping or tightening members which—as a rule—are located at considerable distance from one another.

Other examples of the known art are found described in U.S. Pat. No. 3,795,815 (Weinstock et al.), which teaches a cassette holder fitted to a wheel chair and SE,B,354 728 (Tideström et al.) which teaches a freely transportable device for holding an X-ray film cassette in freely variable positions.

The majority of known arrangements and apparatus have the drawback that a cassette provided with receptor and mounted in a cassette holder can be centered in relation to the radiation source connected only with great difficulty. For instance, it is difficult to position the radiation source in relation to the image receptor so that radiation emitted from said source will pass at right angles to the receptor. Consequently, there is an obvious risk that the images taken will be unsatisfactory and need to be retaken, with subsequent exposure of the patient to unnecessary high dosages of radiation.

These difficulties are accentuated when a grid or screen is placed in the vicinity of the cassette holder—as is normally the case. An important prerequisite with respect to satisfactory images or photographs is that the screen extends perpendicularly to the radiation beam in one plane.

SUMMARY OF THE INVENTION

The object of the present invention is to provide a method and an arrangement which will avoid the majority of the aforesaid drawbacks encountered with known methods and arrangements in respect of the majority of handicapped patients who are unable to leave their beds unaided but who, nevertheless, are able to assume a sitting position in bed, possibly with the assistance of attending personnel.

The inventive method is of the kind defined in the preamble of the following claim 1 and is characterized by the features set forth in the characterizing clause of said claim.

The inventive method enables various types of images to be taken without noticeable discomfort to the patient and without impediment to movement of the cassette holder between different, relevant setting positions. Precise centering of the receptor in relation to the radiation source is also achieved, and only negligible adjustments to the position or attitude of the patient are needed, these adjustments being easily managed by the attendant personnel. The small positional changes required are more related to exposures to be taken with patients of different sizes.

Another small movement normally required of a patient is related to the necessity of taking an exposure with the patient leaning slightly forwards. The patient can straighten his/her back slightly, when the cassette holder is passed in the aforesaid circuit path between the various exposure positions.

The automatic guiding of the cassette holder can be effected with the aid of a parallel linkage mechanism which is mounted in an appropriate manner in relation to the cassette holder and the attachment of said pivotal arm or arms and which will provide the movement desired.

The cassette-holder may be self-locking on the end of the pivotal arm or arms, i.e. so as to ensure that the position to which the cassette holder is adjusted will remain unchanged until a force of given value is applied.

It is preferred in practice, however, that the cassette holder is fixated in a desired position of adjustment with the aid of a finger-operated fixating device which is released prior to commencement of said pivotal movement.

According to a second aspect, the invention also relates to a cassette-holder device for X-ray or like examination, said cassette-holder device having the characteristic feature set forth in the following claim 3.

An exemplifying embodiment of the invention will now be described with reference to the accompanying drawings.

BRIEF DESCRIPTION OF THE DRAWINGS

FIG. 1 is a perspective view of a cassette-holder device constructed in accordance with the invention, and shows the device is coaction with a radiation source for the exposure of an X-ray picture on a bed-sitting patient.

FIG. 2 is a view from above of the holder device illustrated in FIG. 1.

DESCRIPTION OF PREFERRED EMBODIMENTS

Figure 3:
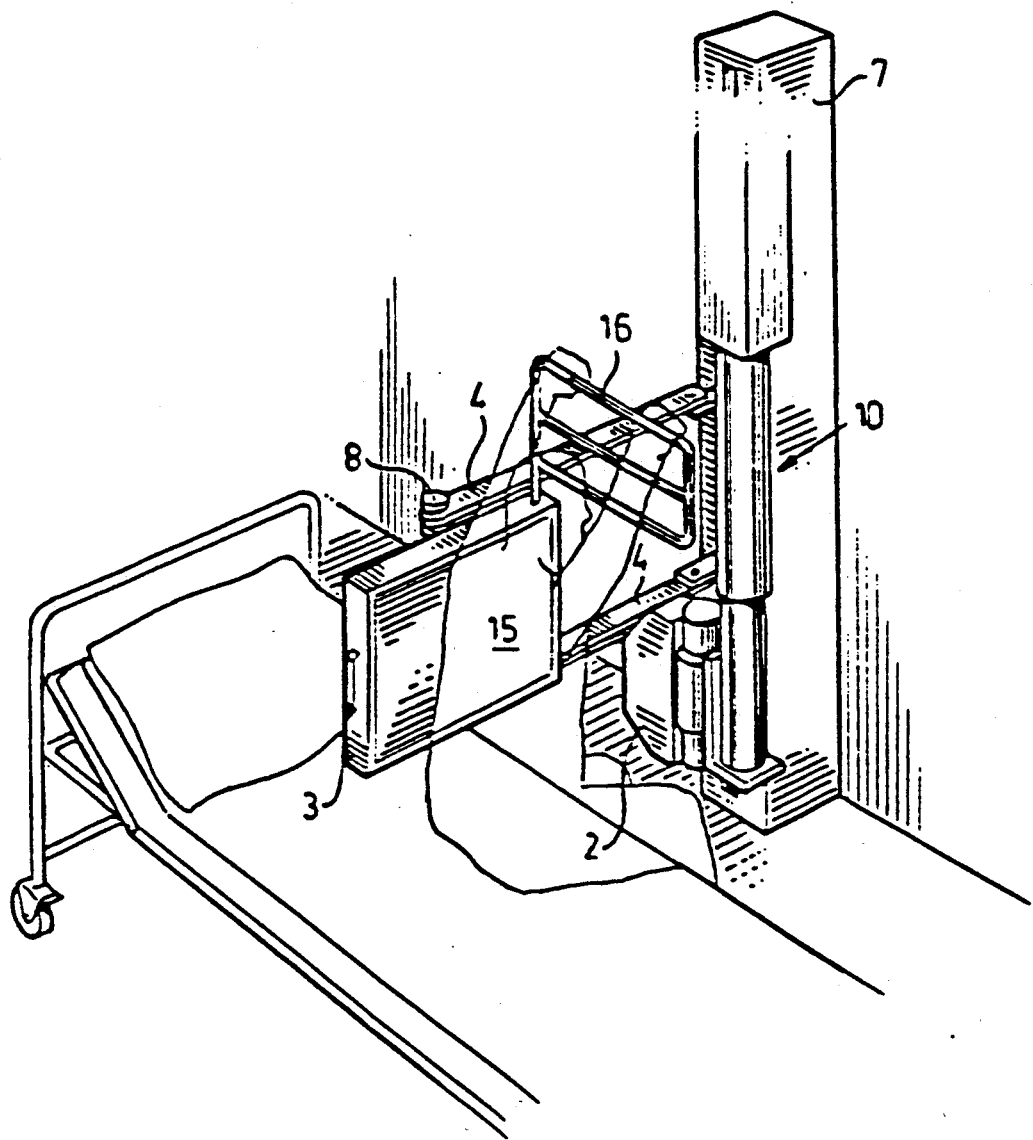
FIG. 3, finally, is a perspective view of a holder device and radiation source according to FIG. 1 when taking a side-exposure of the patient, i.e. in a direction which is 90° to the direct shown in FIG. 1.

The reference numeral 1 in the various Figures of the drawings identifies a cassette-holder device for X-ray or like examination. The cassette-holder device is intended for coaction with a radiation source 2 carried by a telescopic, ceiling-mounted frame 10.

The cassette-holder itself is referenced 3 and comprises a so-called potter or bucky box which is intended to receive replaceably and to center with receptor-equipped cassettes of mutually different sizes.

The cassette holder 3 is mounted on an upper and a lower pivotal arm 4, each of said arms being pivotally connected at one end thereof to a respective holder element 5 extending from a central slot 7a in a column structure 7.

The holder elements 5 form part of a counter-balanced hoist arrangement which enables the cassette holder device to be positioned in the vertical direction.

The outer ends of respectively pivotal arms 4 are connected to the cassette holder, approximately in the center of said holder, by means of a pivot axle 4b.

The cassette holder can be releasably locked in desired positions relative to the arms 4, with the aid of a locking device in the form of a knob 8.

Extending perpendicularly from the lower side of the cassette holder 3 is a shoulder 6 which is connected to the lower element 5 projecting from the column structure 7, by means of a parallel linkage 11. The parallel linkage 11 is connected to respective elements 5 and 6 via pivot axles 5a and 6a respectively. The parallel linkage 11 therewith forms a parallel mechanism which is operative to guide the cassette holder in a predetermined path upon activation of one of the pivotal arms 4 between the two positions illustrated in chain lines in FIGS. 1 and 2 and forming an angle of 90° with one another.

The position of the cassette holder illustrated in FIGS. 1 and 2, where said holder is parallel with the wall, can be said to constitute a "parking position", i.e. a position in which the cassette holder is out of the way.

A conventional exposure position for taking a photograph of the lungs of a sitting patient 15 is shown in full lines in FIGS. 1 and 2. The patient is shown seated in a forwardly inclined position.

The cassette holder is then moved to the position illustrated in FIG. 3 for taking a side picture, by activation of the arm 4. In doing so, the locking knob 8 is first released, so that the arm 4 can be swung. The parallel linkage mechanism 11 assists in enabling the cassette holder to be moved in a circuit path around the patient 15, to the position illustrated in FIG. 3, i.e. without discomfort to the patient.

As illustrated in FIG. 3, the cassette holder is provided with a handle or hand grip 16. The patient grips the handle, as shown in FIG. 3, so that the patient will be brought to a correct position in relation to the image receptor concerned, more or less automatically. It may be necessary, in this respect, for the patient to adjust his/her position slightly, in order to enable a picture of the best possible quality to be taken. The X-ray operator assists the patient in making these movements, which can therewith can be performed without undue difficulty.

When the cassette holder has been brought to the position illustrated in FIG. 3, the knob 8 is turned so as to lock the cassette in its adjusted position.

The handle 16 is removably attached to the cassette holder, and can be removed when not needed.

I claim:

1. A method for performing X-ray examination with the use of a cassette-carried receptor intended to receive radiation from a radiation source which is set to take two or more pictures of a patient in exposure positions in at least approximately perpendicular directions, said cassette being detachably received in a holder which is carried by a frame structure and which can be adjusted positionally in a vertical direction, characterized by pivotally mounting the cassette holder on the end of one or more pivotal arms which can be swung in the horizontal plane; and activating said pivotal arm or arms such as to move the cassette holder between the various exposure positions while automatically guiding the holder in a circuit path past a sitting patient.

2. A method according to claim 1, characterized by releasably locking the cassette holder to the pivotal arm in said exposure positions.

3. A cassette holder device for X-ray examination with the aid of a cassette-carried receptor intended for receiving radiation from a radiation source (2), said cassette being removably located in a holder (3) which is carried by carrier means (4) on a frame structure (7) for vertical adjustment in relation to said frame structure, characterized in that the carrier means includes at least one arm (4) which can be pivoted in the horizontal plane and which is pivotally connected at one end thereof to the cassette holder (3) so that when taking pictures in at least approximately perpendicular directions on a sitting patient (15), it can be moved between the exposure positions in a circuit path past the patient.

4. A cassette holder device according to claim 3, characterized in that the cassette holder (3) is carried by an upper and a lower arm (4) which engage approximately centrally with two mutually opposing sides of the cassette holder (3).

5. A cassette holder device according to claim 4 characterized by means (8) for releasably locking the cassette holder in relation to one of the arms (4).

6. A cassette holder device according to claim 3, characterized by a parallel linkage (11) which is operative to guide the cassette holder (3) in said path when the arm (4) is pivoted.

7. A cassette holder device according to claim 3, characterized by a detachably mounted element (16) on the cassette holder by means of which the cassette holder can be gripped by said patient while an exposure is taken.

8. A cassette holder device according to claim 3, characterized by an element mounted on the cassette holder by means of which the cassette holder can be gripped by said patient while an exposure is taken.

* * * * *